United States Patent [19]

Ravichandran

[11] Patent Number: 5,026,750
[45] Date of Patent: Jun. 25, 1991

[54] 1-HYDROCARBYLOXY HINDERED AMINE MERCAPTOACID ESTERS, THIOACETALS, SULFIDES AND DISULFIDES

[75] Inventor: Ramanathan Ravichandran, Nanuet, N.Y.

[73] Assignee: Ciba-Geigy Corporation, Ardsley, N.Y.

[21] Appl. No.: 479,908

[22] Filed: Feb. 14, 1990

Related U.S. Application Data

[63] Continuation-in-part of Ser. No. 326,348, Mar. 21, 1989, abandoned.

[51] Int. Cl.$^5$ .......................... C08K 5/34; C08K 5/35; C07D 211/34; C07D 211/40; C07D 211/54
[52] U.S. Cl. ........................ 524/99; 524/102; 524/103; 546/16; 546/187; 546/188; 546/193; 546/194; 546/214
[58] Field of Search ............... 546/187, 188, 193, 194, 546/214, 16; 524/99, 102, 103

[56] References Cited

U.S. PATENT DOCUMENTS 4,102,858  7/1978  Minagawa et al. ................. 524/102
4,665,185  5/1987  Winter et al. ...................... 546/189

OTHER PUBLICATIONS

Shlyapintokh et al., "Antioxidant Action of Sterically Hindered Amines and Related Compounds", *Developments in Polymer Stabilisation*, V, Applied Science Publishers, New Jersey, 1982.

*Primary Examiner*—Kriellion Morgan
*Attorney, Agent, or Firm*—Luther A. R. Hall

[57] ABSTRACT

1-Hydrocarbyloxy hindered amine mercaptoacid esters, thioacetals, sulfides and disulfides are effective light stabilizers for protecting a variety of polymer substrates from the deleterious effects of actinic light.

22 Claims, No Drawings

1-HYDROCARBYLOXY HINDERED AMINE MERCAPTOACID ESTERS, THIOACETALS, SULFIDES AND DISULFIDES

This is a continuation-in-part application of application Ser. No. 326,348, filed on March 21, 1989, now abandoned.

The instant invention pertains to 1-hydrocarbyloxy hindered amine campounds which are esters of mercaptoacids, thioacetals, sulfides and disulfides and to polymer compositions stabilized against the deleterious effects of actinic light by the presence of said compounds.

BACKGROUND OF THE INVENTION

U.S. Pat. No. 3,939,170 describes hindered amine derivatives which are the 4-(2,2,6,6,-tetramethyl-1,2,3,6-tetrahydropyridine) sulfide, sulfoxide and sulfone as well as the compounds substituted on the N-atom by oxyl or hydroxy.

Substituted thiocarboxylate esters containing hindered amine moieties are disclosed in U.S. Pat. No. 4,102,858, but in none of these esters does the hindered amine N-atom bear a hydrocarbyloxy group.

The instant compounds clearly differ structurally from these prior art materials.

DETAILED DISCLOSURE

The instant invention is to 1-hydrocarbyloxy hindered amine derivatives having the formula

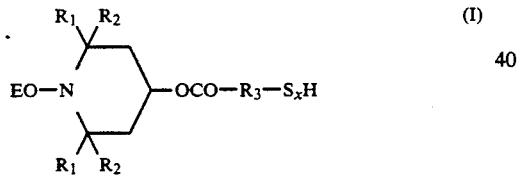

(I)

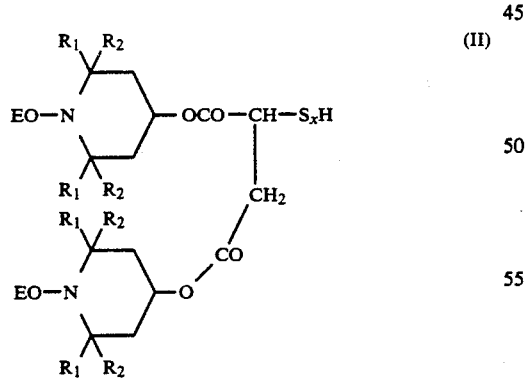

(II)

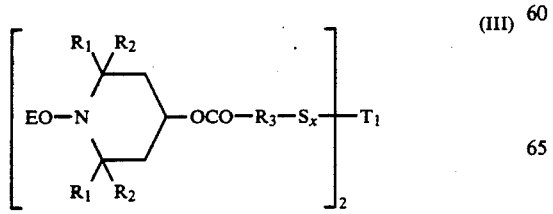

(III)

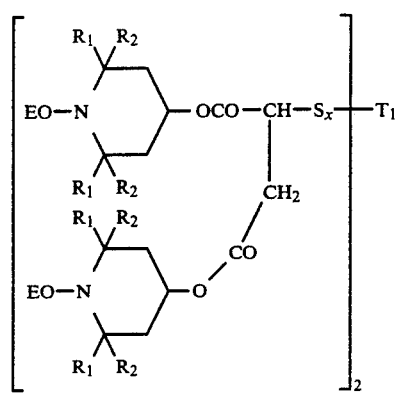

(IV)

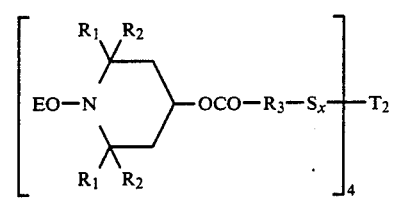

(V)

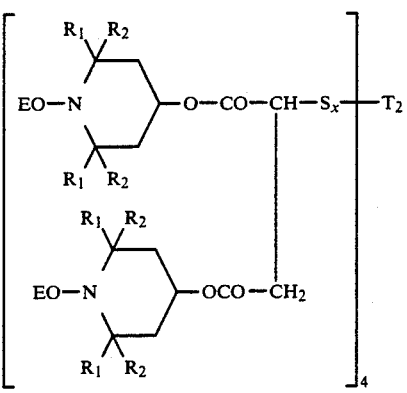

(VI)

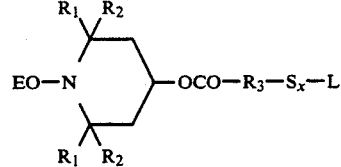

(VII)

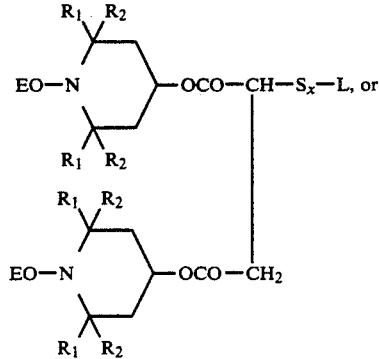

(VIII)

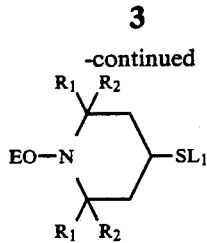

where
x is 1 or 2,
R₁ and R₂ are independently methyl or ethyl, or R₁ and R₂ together are pentamethylene,
R₃ is alkylene of 1 to 3 carbon atoms,
E is alkyl of 1 to 18 carbon atoms, cycloalkyl of 5 to 12 carbon atoms, alkenyl of 3 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl,
T₁ is 1,1-alkylidene of 1 to 18 carbon atoms, 1,1-cycloalkylidene of 5 to 12 carbon atoms, benzylidene, 3,5-di-tert-butyl-4-hydroxybenzylidene or naphthal,
T₂ is

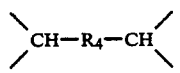

where R₄ is a direct bond, alkylene of 1 to 10 carbon atoms or arylene of 6 to 10 carbon atoms, and

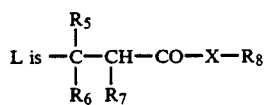

where R₅ is hydrogen, methyl or phenyl,
R₆ is hydrogen or methyl
R₇ is hydrogen, alkyl of 1 to 4 carbon atoms, —CH₂CO—X—R₈, —CH₂CH₂CO—X—R₈ or —CH(CH₃)CO—X—R₈,
X is —O— or —NR₈—,
R₈ is hydrogen, alkyl of 1 to 18 carbon atoms, aralkyl of 7 to 15 carbon atoms, cycloalkyl of 5 to 12 carbon atoms,

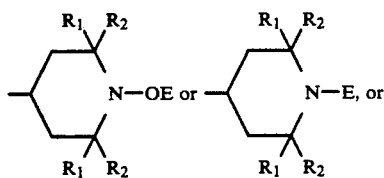

L is —CH₂CH₂CN or —CH₂CH₂PO(OR₉) where R₉ is alkyl of 1 to 4 carbon atoms, or

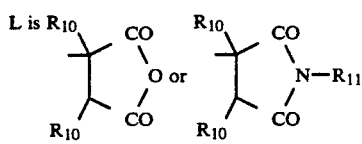

where R₁₀ is hydrogen or methyl,
R₁₁ is alkyl of 1 to 8 carbon atoms or phenyl, and
L₁ is hydrogen or has the same meaning as L.
Preferably R₁ and R₂ are each methyl.
R₃ is preferably methylene or ethylene.
E is preferably alkyl of 1 to 12 carbon atoms, cyclohexyl, or alpha-methylbenzyl; most preferably methyl, octyl, nonyl, cyclohexyl or alpha-methylbenzyl.
T₁ is preferably 1,1-alkylidene of 4 to 12 carbon atoms, cyclohexylidene, benzylidene or 3,5-di-tert-butyl-4-hydroxybenzylidene.
T₂ is preferably a group where R₄ is a direct bond, methylene or p-phenylene.
Preferably L is a group of formula X wherein R₅ and R₆ are each hydrogen, R₇ is hydrogen or methyl, X is —O—, and R₈ is alkyl of 1 to 8 catbon atoms; most preferably R₈ is alkyl of 1 to 4 carbon atoms.

Synthesis

The compound of this invention are prepared from the 1-hydrocarbyloxy-2,2,6,6-tetramethylpiperidin-4-yl esters of mercapto acids. These esters are reacted with alpha,beta-unsaturated carbonyl compounds to add across the double bond in a Michael addition or are reacted with aldehydes to form the corresponding thioacetals.

The 1-hydrocarbyloxy-2,2,6,6-tetramethylpiperidin-4-yl esters are made by conventional methods from the corresponding alcohol.

The intermediate hindered amine alcohol is an item of commerce as are the mercapto acids.

Hydroxylamines are conveniently prepared by the oxidation of amines to the N-oxyl intermediates using hydrogen peroxide as taught by E. G. Rozantsev et al, Synthesis, 1971, 190; or by an organic hydroperoxide and metal oxide catalyst followed by catalytic hydrogenation (U.S. Pat. No. 4,665,185).

The N-hydrocarbyloxy hindered amines are prepared by several routes. N-Methoxy derivatives are prepared by reaction of an N-oxyl compound with methyl radicals generated from the thermolysis of di-tert-butyl peroxide in an inert solvent such as chlorobenzene.

N-Hydroxy derivatives can be alkylated by reaction with sodium hydride and an alkyl halide. A preferred method for preparing N-hydrocarbyloxy compounds involves the thermal reaction of a hydrocarbon solution of a hindered amine or its N-oxyl derivative with tert-butyl hydroperoxide and a metal oxide catalyst as taught in copending patent application Ser. No. 259,949.

The alpha,beta-unsaturated carbonyl intermediates are largely items of commerce.

Typical alpha,beta-unsaturated carbonyl intermediates are the esters, amides, acids, imides and ketones typified by the acrylates, methacrylates, cinnamates, tiglates, crotonates, itaconates, citraconates, senecioates (=dimethylacrylates), maleates, fumarates, maleimides and the like.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

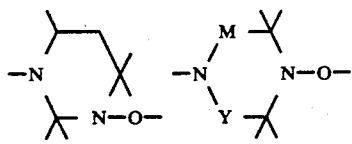

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/ isobutylene, ethylene/butene-1, propylene/butadiene, isobutylene/isoprene, ethylene/alkyl acrylates, ethylene/ alkyl methacrylates, ethylene/vinyl acetate or ethylene/ acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/ propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/ vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone -acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example, 2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example, 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate 3,5-di-tert-butyl-4-hydroxybenzyl-phosphoric acid dioctadecyl ester 3,5-di-tert-butyl-4-hydroxybenzyl-phosphoric acid monoethyl ester, calcium-salt

1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate

1.7. Esters of
β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of
β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of
β-(3,5-di-tert-butyl-4-hydroxyphenyl)-propionic acid for example, N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine

2. UV absorbers and light stabilizers

2.1. 2-(2'-Hydroxyphenyl)-benzotriazoles for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6,-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6,-tetramethylpiperidyl)-hexamethylenediamine and 4-tert-octylamino-2,6-dichloro-s-triazine, tris-(2,2,6,6,-tetramethylpiperidyl)-nitrilotriacetate, tetrakis-(2,2,6,6,-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of $\beta$-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-($\beta$-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives for example, plasticizers, lubricants, emulsifiers, pigments, optical brighteners, flameproofing agents, antistatic agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/ melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyan-$\beta$,-62 -diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2,'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tertamylphenyl)-2H-benzotriazole, 2-[2-hydroxy-3-tert-butyl-5-(2-(omega-hydroxy-octa-(ethyleneoxy)carbonyl)-ethylphenyl] -2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising (a) an acid catalyzed thermoset coating or enamel based on hot crosslinkable acrylic, polyester or alkyd resins, (b) a NOE-substituted 2,2,6,6-tetraalkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

A further embodiment of the instant invention involves the instant compounds of formula I, II and IX which each contain a free mercapto (-SH) moiety capable of adding across a double bond whether in an alpha,-beta-unsaturated carbonyl compound or across an ethylenically unsaturated bond existing in a polymer substrate. The latter allows the instant stabilizer compound of formula I, II or IX to be grafted onto said polymer substrate thus resisting loss from the substrate by volatilization, exudation, extraction or the like. Polymers having such unsaturated groups in the polymer backbone or structure include the polymers and copolymers such as are mentioned earlier under polymer groups 1, 3, 5, 6, 32, etc. Such polymer substrates are particularly typified by acrylonitrile/butadiene/styrene graft polymers generally referred to as ABS resins.

Another preferred embodiment of the instant invention is the combination of the instant stabilizers with hydroxylamines to protect polypropylene fibers from gas fading.

The following examples are presented for the purpose of illustration only and are not to be construed to limit the nature or scope of the instant invention in any manner whatsoever.

EXAMPLE 1

1-Cyclohexyloxy-2,2,6,6-tetramethylpiperidin-4-yl Thioglycolate

1-Cyclohexyloxy-2,2,6,6-tetramethylpiperidin-4-ol a (25.5 grams, 0.1 mol) and methyl thioglycolate (10.6 grams, 0.11 mol) are dissolved in toluene. Lithium amide (0.09 mol) is added and the reaction mixture is heated under reflux and the distillate collected in a Dean-Stark trap. After heating under reflux overnight, the toluene is removed under reduced pressure. Acetic acid is added to neutralize the basic catalyst. The crude reaction product is purified by liquid chromatography to afford the title compound.

The nmr and mass spectrum data are consistent with the above-named ester.

EXAMPLE 2

1-Octyloxy-2,2,6,6-tetramethylpiperidin-4-yl Thioglycolate

The general procedure of Example 1 is followed using 2.09 grams (7.0 mmol) of 1-octyloxy-4-hydroxy-2,2,6,6-tetramethylpiperidine, 0.74 gram (7.0 mmol) of methyl thioglycolate and 0.17 gram of lithium amide in 50 ml of toluene to afford the title compound after purification by silica gel chromatography.

The nmr and mass spectra data are consistent with the structure of the above-named ester.

EXAMPLE 3

1-Cyclohexyloxy-2,2,6,6-tetramethylpiperidin-4-yl 3-Mercaptopropionate

The general procedure of Example 1 is followed using 2.00 grams (7.8 mmol) of 1-cyclohexyloxy-4-hydroxy-2,2,6,6-tetramethylpiperidine, 0.18 gram of lithium amide and 0.94 gram (7.8 mmol) of methyl 3-mercaptopropionate in 50 ml of toluene to afford the title compound after purification by silical gel chromatography.

The nmr and mass spectra data are consistent with the structure of the above-named ester.

EXAMPLES 4–8

Following the general procedure of Example 1, 1-hydrocarbyloxy-2,2,6,6-tetramethylpiperidin-4-yl esters of a variety of mercapto acids are prepared. Typical such esters are listed in the table below.

| Example | 1-Hydrocarbyloxy Group | Mercaptoacid Ester |
|---|---|---|
| 4 | 1-octyloxy | 3-mercaptopropionate |
| 5 | 1-alpha-methylbenzyloxy | mercaptosuccinate |
| 6 | 1-nonyloxy | thioglycolate |
| 7 | 1-octyloxy | mercaptosuccinate |
| 8 | 1-methoxy | 3-mercaptopropionate |

EXAMPLE 9

1,1-Bis-(1-methoxy-2,2,6,6-tetramethylpiperidin-4-yloxycarbonylmethylthio)octane 1-Octanal is added slowly to a solution of 1-methoxy-2,2,6,6-tetramethylpiperidin-4-yl thioglycolate in toluene at a temperature below 20° C. After stirring the reaction mixture overnight at 70° C., the solvent is removed to yield the title compound.

EXAMPLES 10–16

Following the general procedure of Example 9 when a stoichiometrically appropriate amount of a 1-hydrocarbyloxy-2,2,6,6-tetramethylpiperidin-4-yl ester of a variety of mercapto acids is reacted with a stoichiometrically appropriate amount of an aldehyde, the following instant compounds are prepared.

| Example | 1-Hydrocarbyloxy Group | Mercapto-acid Ester | Aldehyde |
|---|---|---|---|
| 10 | 1-octyloxy | 3-mercapto- | 1-octanal |

| Example | 1-Hydrocarbyloxy Group | Mercapto-acid Ester | Aldehyde |
|---|---|---|---|
| 11 | 1-nonyloxy | propionate thioglycolate | glyoxal |
| 12 | 1-cyclohexyloxy | 3-mercapto-propionate | terephthaldehyde |
| 13 | 1-octyloxy | mercaptosuc-cinate | lauryl aldehyde |
| 14 | 1-methoxy | 3-mercapto-propionate | 3,5-di-tert-butyl-4-hydroxy-benzaldehyde |
| 15 | 1-cyclohexyloxy | thioglycolate | 1-octanal |
| 16 | 1-alpha-methylbenzyloxy | mercaptosuc-cinate | glyoxal |

EXAMPLE 17

Di(1-methoxy-2,2,6,6-tetramethylpiperidin-4-yl) 3,3'-Dithiodipropionate

Oxalyl chloride (2.1 ml) is added to a stirred suspension of 3,3'-dithiodipropionic acid (2.1 grams) and 2 drops of N,N-dimethylformamide in 20 ml of methylene chloride. After stirring at room temperature for four hours, the resulting solution is concentrated under reduced pressure and the residue is dissolved in toluene. The toluene solution of the acid chloride is added dropwise to a stirred solution of 1-methoxy-2, 2,6,6-tetramethylpiperidin-4-ol (3.5 grams) and pyridine (2 ml) at 20°-25° C. After stirring at room temperature for one hour, the reaction mixture is concentrated under reduced pressure and the residue partitioned between methylene chloride and water. The organic layer is dried over anhyrous magnesium sulfate and concentrated. The resulting crude product is chromatographed to afford the title compound as a colorless oil.

Analysis: Calcd for $C_{26}H_{48}N_2O_6S_2$: C, 56.8; H, 8.7; N, 5.1. Found: C, 55.6; H, 8.7; N, 4.9.

EXAMPLES 18–25

When following the general procedure of Example 17, a 1-hydrocarbyloxy-2,2,6,6-tetramethylpiperidin-4-ol is reacted with an acid chloride of a thio or dithio dialkanoic acid, the following instant compounds are prepared.

| Example | 1-Hydrocarbylox Group | Acid |
|---|---|---|
| 18 | 1-octyloxy | 3,3'-thiopropionic |
| 19 | 1-cyclohexyloxy | thiodiglycolic |
| 20 | 1-nonyloxy | 4,4'-dithiodibutyric |
| 21 | 1-alpha-methylbenzyloxy | 3,3'-dithiodipropionic |
| 22 | 1-octyloxy | thiodiglycolic |
| 23 | 1-methoxy | 4,4'-dithiodibutyric |
| 24 | 1-cyclohexyloxy | 3,3'-dithiodipropionic |
| 25 | 1-octyloxy | 3,3'-dithiodipropionic |

EXAMPLE 26–36

When a 1-hydrocarbyloxy-2,2,6,6-tetramethylpiperidin-4-yl ester of a variety of mercapto acids, as prepared in Examples 1–8, is reacted with an alpha,beta-unsaturated ester, acid, anhydride, imide, cyano or similar compound under conditions favoring the Michael addition of the mercapto group across the double bond, as in the presence of an acid or basic catalyst, the following instant compounds are prepared.

| Example | 1-Hydrocarbyloxy Group | Mercaptoacid Ester | alpha,beta-Unsaturated Compound |
|---|---|---|---|
| 26 | 1-octyloxy | thioglycolate | diethyl maleate |
| 27 | 1-nonyloxy | thioglycolate | methyl acrylate |
| 28 | 1-cyclohexyloxy | mercaptosuccinate | dimethyl itaconate |
| 29 | 1-methoxy | 3-mercaptopropionate | maleic anhydride |
| 30 | 1-octyloxy | mercaptosuccinate | N-methylmaleimide |
| 31 | 1-nonyloxy | 3-mercaptopropionate | methyl vinyl-ketone |
| 32 | 1-methoxythio | glycolate | N-phenylmaleimide |
| 33 | 1-octyloxy | 3-mercaptopropionate | dibutyl maleate |
| 34 | 1-cyclohexyloxy | thioglycolate | acrylonitrile |
| 35 | 1-octyloxy | thioglycolate | diethyl vinyl phosphonate |
| 36 | 1-alpha-methylbenzyloxy | 3-mercaptopropionate | maleic acid |

EXAMPLE 37

Light Stabilization of Polypropylene

This example illustrates the light stabilizing effectiveness of instant stabilizers.

Polypropylene (Himont Profax 6501) powder stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
|---|---|---|
| Control* | — | 340 |
| Example 17 | 0.1 | 1020 |

*Base resin plus 0.1% calcium stearate and 0.2% of n-octadecyl 3,5-di-tert-butyl-4-hydroxyhydrocinnamate.

EXAMPLE 38

Stabilization of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4"×12" (10.16 cm×30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

EXAMPLE 39

To a sample of unpigmented acrylonitrile/butadiene/styrene (ABS) resin is added 0.5% by weight of a compound of Example 1. The stabilized composition is then injection molded to form a thin sheet of 0.125 inch (0.32 cm) thickness. A portion of the sheet is exposed to accelerated weathering in a QUV exposure apparatus and 20° gloss values of the sheet are determined before and after exposure.

The loss of gloss of the stabilized sheet is considerably less than that of an unstabilized control sheet.

Another portion of the stabilized sheet after injection molding is extracted with toluene to ascertain whether the stabilizer of Example 1 is bound to the polymer substrate or whether it is extractable. Essentially none of the stabilizer compound of Example 1 is extracted from the molded ABS resin into the toluene indicating that the stabilizer itself is grafted onto the ABS substrate resin.

What is claimed is:

1. A compound which is a 1-hydrocarbyloxy hindered amine derivative having the formula

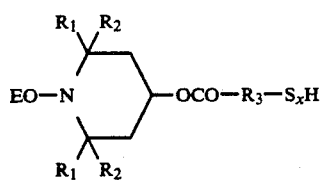
(I)

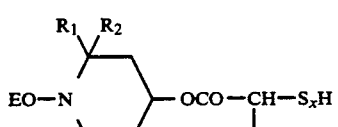
(II)

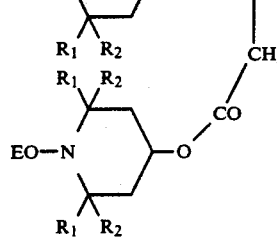

-continued

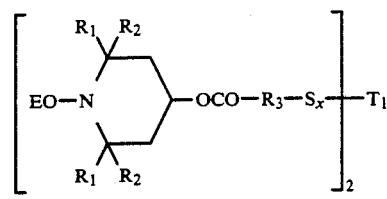
(III)

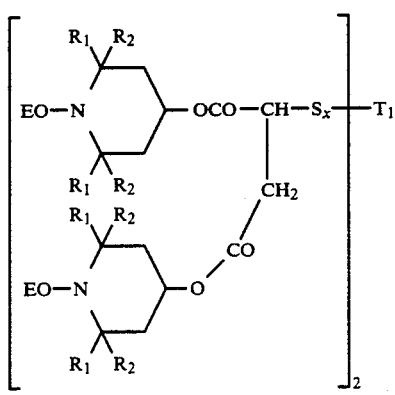
(IV)

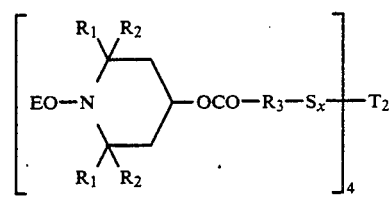
(V)

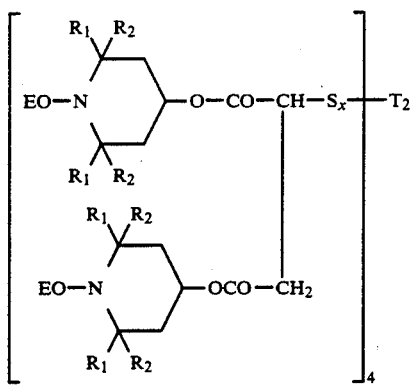
(VI)

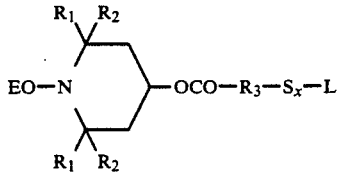
(VII)

-continued

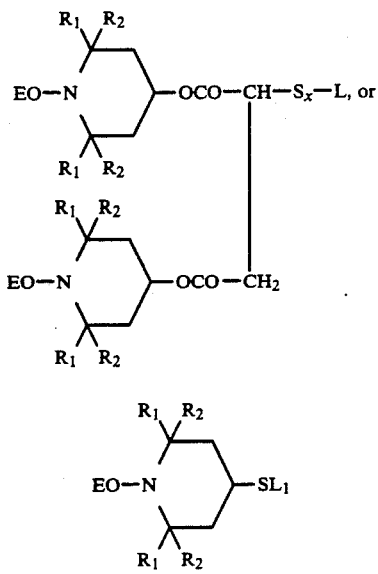

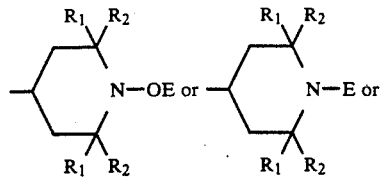

L is —CH$_2$CH$_2$CN or —CH$_2$CH$_2$PO(OR$_9$) where R$_9$ is alkyl of 1 to 4 carbon atoms, or

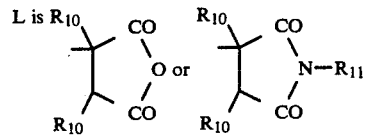

where R$_{10}$ is hydrogen or methyl,
R$_{11}$ is alkyl of 1 to 8 carbon atoms or phenyl, and
L$_1$ is hydrogen or has the same meaning as L.

2. A compound according to claim 1 wherein R$_1$ and R$_2$ are each methyl.

3. A compound according to claim 1 wherein R$_3$ is methylene or ethylene.

4. A compound according to claim 1 wherein E is alkyl of 1 to 12 carbon atoms, cyclohexyl or alpha-methylbenzyl.

5. A compound according to claim 4 wherein E is methyl, octyl, nonyl, cyclohexyl or alpha-methylbenzyl.

6. A compound according to claim 1 wherein R$_1$ is 1,1-alkylidene of 4 to 12 carbon atoms, cyclohexylidene, benzylidene or 3,5-di-tert-butyl-4-hydroxybenzylidene.

7. A compound according to claim 1 wherein T$_2$ is a group where R$_4$ is a direct bond, methylene or p-phenylene.

8. A compound according to claim 1 wherein L is a group of formula X wherein R$_5$ and R$_6$ are both hydrogen, R$_7$ is hydrogen or methyl, X is —O—, and R$_8$ is alkyl of 1 to 8 carbon atoms.

9. A compound according to claim 8 wherein R$_8$ is alkyl of 1 to 4 carbon atoms.

10. The compound according to claim 1 which is 1-cyclohexyloxy-2,2,6,6-tetramethylpiperidin-4-yl thioglycolate.

11. The compound according to claim 1 which is 1,1-bis-(1-methoxy-2,2,6,6-tetramethylpiperidin-4-yloxycarbonylmethylthio)octane.

12. The compound according to claim 1 which is di-(1-methoxy-2,2,6,6-tetramethylpiperidin-4-yl) 3,3'-dithiodipropionate.

13. The compound according to claim 1 which is 1-octyloxy-2,2,6,6-tetramethylpiperidin-4-yl thioglycolate.

14. The compound according to claim 1 which is 1-cyclohexyloxy-2,2,6,6-tetramethylpiperidin-4-yl 3-mercaptopropionate.

15. A composition stabilized against the deleterious effects of actinic light which comprises
(a) a polymer subject to the deleterious effects of actinic light, and
(b) an effective stabilizing amount of a compound according to claim 1.

16. A composition according to claim 15 wherein the polymer is a polyolefin.

where
X is 1 or 2,
R$_1$ and R$_2$ are independently methyl or ethyl, or R$_1$ and R$_2$ together are pentamethylene,
R$_3$ is alkylene of 1 to 3 carbon atoms,
E is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl,
T$_1$ is 1,1-alkylidene of 1 to 18 carbon atoms, 1,1-cycloalkylidene of 5 to 12 carbon atoms, benzylidene, 3,5-di-tert-butyl-4-hydroxybenzylidene or naphthal,
T$_2$ is

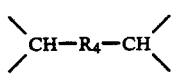

where R$_4$ is a direct bond, alkylene of 1 to 10 carbon atoms or arylene of 6 to 10 carbon atoms, and

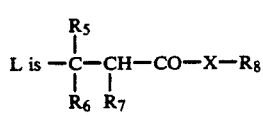

where R$_5$ is hydrogen, methyl or phenyl,
R$_6$ is hydrogen or methyl
R$_7$ is hydrogen, alkyl of 1 to 4 carbon atoms, —CH$_2$CO—X—R$_8$, —CH$_2$CH$_2$CO—X—R$_8$ or —CH(CH$_3$)CO—X—R$_8$,
X is —O— or —NR$_8$—,
R$_8$ is hydrogen, alkyl of 1 to 18 carbon atoms, aralkyl of 7 to 15 carbon atoms, cycloalkyl of 5 to 12 carbon atoms, 17. A composition according to claim 16 wherein the polyolefin is polypropylene.

18. A composition according to claim 15 wherein the compound of component (b) is di(1-methoxy-2,2,6,6-tetramethylpiperidin-4-yl) 3,3'-dithiodipropionate.

19. A composition according to claim 15 wherein the polymer is a coating system based on alkyd, acrylic, acrylic alkyd, polyester, epoxide, urethane, polyamide, vinyl or epoxy-polyester resins.

20. A composition according to claim 15 which contains a UV absorber or additional light stabilizer.

21. A method for stabilizing an synthetic polymer against oxidative, thermal or actinic degradation which comprises incorporating into said synthetic polymer an effective stabilizing amount of a compound according to claim 1.

22. A composition according to claim 15 wherein the polymer contains ethylenically unsaturated double bonds in the polymer structure, and component (b) is a compound which contains a free -SH group.

* * * * *